United States Patent
Kameda et al.

(10) Patent No.: US 7,737,203 B2
(45) Date of Patent: Jun. 15, 2010

(54) MERCAPTOSILANE BLOCKED WITH VINYL ETHER GROUP (COUPLING AGENT) AND RUBBER COMPOSITION AND PNEUMATIC TIRE USING THE SAME

(75) Inventors: Yoshihiro Kameda, Hiratsuka (JP); Misaki Matsumura, Hiratsuka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 0 days.

(21) Appl. No.: 12/299,824

(22) PCT Filed: May 10, 2007

(86) PCT No.: PCT/JP2007/060090
§ 371 (c)(1),
(2), (4) Date: Nov. 6, 2008

(87) PCT Pub. No.: WO2007/132909
PCT Pub. Date: Nov. 22, 2007

(65) Prior Publication Data
US 2009/0137730 A1    May 28, 2009

(30) Foreign Application Priority Data
May 11, 2006    (JP) ............................. 2006-132637

(51) Int. Cl.
*B60C 1/00* (2006.01)
*C08G 18/67* (2006.01)
(52) U.S. Cl. ..................................... 524/262; 524/580

(58) Field of Classification Search .................. 524/262
See application file for complete search history.

(56) References Cited

U.S. PATENT DOCUMENTS

| 6,608,125 B2 | 8/2003 | Cruse et al. |
| 2006/0063878 A1 * | 3/2006 | Sandstrom et al. .......... 524/492 |

FOREIGN PATENT DOCUMENTS

| EP | 1500679 A1 | 1/2005 |
| JP | 05051485 | 3/1993 |
| JP | 09111044 | 4/1997 |
| JP | 2003055353 | 2/2003 |
| JP | 2005171159 | 6/2005 |
| JP | 2005171159 A * | 6/2005 |
| JP | 2006097024 | 4/2006 |

OTHER PUBLICATIONS

Translation of JP 2005171159, Jun. 2005.*
Office Action issued Feb. 25, 2010 from the German Patent Office for corresponding German Patent Application No. 112007001162.9.

* cited by examiner

Primary Examiner—Ling-Siu Choi
Assistant Examiner—Hui Chin
(74) *Attorney, Agent, or Firm*—Connolly Bove Lodge & Hutz LLP

(57) ABSTRACT

A rubber composition, superior in the processability and rubber properties compared with a rubber composition using a conventional mercaptosilane coupling agent, containing 100 parts by weight of a diene-based rubber, 10 to 160 parts by weight of a reinforcing filler containing silica and 0.1 to 20% by weight, based upon the weight of silica, of a mercaptosilane coupling agent blocked with a compound having a vinyl ether group and a pneumatic tire using the same.

12 Claims, No Drawings

MERCAPTOSILANE BLOCKED WITH VINYL ETHER GROUP (COUPLING AGENT) AND RUBBER COMPOSITION AND PNEUMATIC TIRE USING THE SAME

TECHNICAL FIELD

The present invention relates to a silane coupling agent having a mercapto group of mercaptosilane blocked with a vinyl ether group and to a rubber composition and pneumatic tire using the same. More specifically, it relates to a rubber composition comprising a diene-based rubber, in which silica is compounded, which is superior in both of the processability and silica dispersability obtained by using a specific silane coupling agent having a mercapto group of mercaptosilane blocked with a vinyl ether group and a pneumatic tire using the same.

BACKGROUND ART

In the past, in the rubber industry, the technique has been adopted of compounding carbon black as a reinforcing filler to reinforce the rubber, but when carbon black is compounded, there were the problems that the heat buildup of the rubber became higher and that, since the raw materials are derived from petroleum, the environmental load became larger. To solve these problems, in recent years, silica has been compounded as a filler (see Japanese Patent Publication (A) No. 05-51485). However, it is known that silica deteriorates the mixability because of easy agglomeration of silica particles due to the surface characteristics thereof. Therefore, it is known in the art that a silane coupling agent is combinedly used with silica when mixed with rubber with a good dispersability (see Japanese Patent Publication (A) No. 09-111044), but there is still room for improvement. In particular, a conventional silane coupling agent (e.g., mercaptosilane) greatly improves the dispersability of silica in the rubber. The resultant physical properties are also good, but there is the problem that there is a difficulty in the processability. As a technology for blocking the thiol parts of mercaptosilane, there is the technology of blocking with octanoic acid (U.S. Pat. No. 6,608,125). However, this largely decreases the reactivity of the mercapto groups. Although the octanoic acid is not detached at the vulcanization stage and the processing performance is good, this does not largely contribute to the physical properties after the vulcanization. Furthermore, there is the technology that a thiol compound and vinyl ethers are brought into contact to obtain a thiol compound derivative (see Japanese Patent Publication (A) No. 2003-055353). The inclusion of two or more thiol groups is preferable. When reacting with silica, the bound rubber structure around the silica becomes too hard and the resultant compound becomes unpreferable as a rubber composition for a tire.

DISCLOSURE OF THE INVENTION

Accordingly, an object of the present invention is to provide a silica-containing diene-based rubber composition having higher physical properties, capable of improving the processability (i.e., longer scorch time and shorter vulcanization time), and improving reinforcing performance (i.e., improved reinforcing performance index of M300/M100), when compound with conventional mercaptosilane.

In accordance with the present invention, there is provided a mercaptosilane coupling agent blocked with a compound having a vinyl ether group of the formula (I):

wherein A is an oxygen or sulfur atom, $R^1$ and $R^3$ are, independently, a hydrogen atom, a $C_1$ to $C_{18}$, preferably a $C_1$ to $C_{10}$ alkyl group, or a phenyl group, $R^2$ is a $C_1$ to $C_{18}$, preferably $C_1$ to $C_{10}$ alkyl group, $C_2$ to $C_{18}$, preferably $C_2$ to $C_{10}$ alkenyl group, a $C_2$ to $C_{18}$ alkynyl group, or a phenyl group.

In accordance with the present invention, there are provided a rubber composition containing 100 parts by weight of a diene-based rubber, 10 to 160 parts by weight of a reinforcing filler containing silica and 0.1 to 20% by weight, based upon the weight of the silica, of a mercaptosilane coupling agent blocked with a compound having a vinyl ether group and a pneumatic tire using the same.

EFFECTS OF THE INVENTION

The present invention uses, as the silane coupling agent component compounded into the silica-containing rubber composition, a mercaptosilane coupling agent blocked with a compound having a vinyl ether group, whereby while the conventional good silica dispersability is maintained, the processability is further improved and, furthermore, the amount of sulfur in a molecule is increased to thereby increase the cross-linking density and, as a result, the rubber physical properties can be improved.

BEST MODE FOR CARRYING OUT THE INVENTION

The inventors engaged in research to solve the above problem and, as a result, succeeded in maintaining the silica dispersability of the rubber composition and improving the processability by blocking a mercaptosilane coupling agent containing a mercapto group with a compound having a vinyl ether group of the formula (I), followed by compounding into a silica-containing rubber composition.

The rubber composition of the present invention is obtained by compounding, into 100 parts by weight of the diene-based rubber, 10 to 160 parts by weight of a reinforcing filler containing silica and 0.1 to 20% by weight, based upon the weight of silica, of a mercaptosilane coupling agent blocked with a compound having a vinyl ether group.

As the diene-based rubber usable in the present invention, any diene-based rubber capable of using for tire may be used. Specifically, natural rubber (NR), styrene-butadiene copolymer rubbers (SBR), polyisoprene rubbers (IR), polybutadiene rubbers (BR), butyl rubbers (IIR), ethylene-propylene-diene copolymer rubbers, etc. may be exemplified. These may be used alone or in any blends thereof. Note that NR, SBR and BR may be modified in their main chains or ends with, for example, an alkoxyl group or a carbonyl group, a hydroxyl group, an epoxy group, or other functional groups having a high affinity with silica, etc.

The reinforcing filler usable in the present invention is compounded, by an amount, based upon 100 parts by weight of the diene-based rubber, of 10 to 160 parts by weight, preferably 50 to 140 parts by weight, more preferably 60 to 120 parts by weight. If this amount is too small, there is little effect for reinforcing the rubber, while conversely if too large, the mixability of the rubber and the filler is remarkably decreased, and, therefore, this is not preferred. The reinforcing filler is at least one member selected from the groups consisting of carbon black, silica, aluminum hydroxide, clay, calcium carbonate, titanium oxide, etc., but in the present invention, the amount of the silica has to be 10 to 120 parts by weight, 20 to 90 parts by weight is preferable. If the amount of the silica is too small, the desired effect is liable not to be obtained, while conversely if too large, the scorch property is liable to be deteriorated.

The mercaptosilane coupling agent blocked with a compound having a vinyl ether group used in the present invention can be obtained, for example, by reacting the mercaptosilane shown in the above formula (II) or (III) with a compound having a vinyl ether group shown by the formula (I) together with, for example, a phosphoric acid ester catalyst, etc. The blocked mercaptosilane is compounded in an amount, based upon the weight of silica, of 0.1 to 20% by weight, preferably 2 to 14% by weight. If the compounding amount is too small, the compounding effect is not sufficient, while conversely if too large, the scorch property and, the processability are deteriorated, and an increase in the cost is also invited, and therefore, this is not preferred.

wherein $R^4$ and $R^5$ are, independently, a $C_1$ to $C_{18}$, preferably $C_1$ to $C_{10}$ linear or branched alkyl group and/or a $C_1$ to $C_{18}$, preferably $C_2$ to $C_{15}$ alkyl group having an ether skeleton, $R^6$ is a $C_1$ to $C_8$, preferably $C_1$ to $C_4$ alkylene group and n is 0, 1, or 2, preferably 0.

wherein $R^7$ is a $C_1$ to $C_8$, preferably $C_1$ to $C_4$ linear or branched alkylene group, $R^3$ to $R^{10}$ are, independently, a $C_1$ to $C_{18}$ preferably $C_1$ to $C_{10}$ linear or branched alkyl group and/or $C_1$ to $C_{18}$, preferably $C_2$ to $C_{15}$ alkyl group having an ether skeleton.

In another aspect of the present invention, the mercaptosilane coupling agent shown by the formula (II) or (III) may be blocked with a compound having a vinyl ether group having the formula (I), preferably polyhydric vinyl ether, to obtain the desired mercaptosilane coupling agent. As such polyhydric vinyl ethers, for example, divinyl ether, trivinyl ether, tetravinyl ether, etc. may be mentioned. These polyhydric vinyl ethers may, for example, be reacted, together with a phosphoric acid ester catalyst etc., with a mercaptosilane coupling agent so as to block the mercapto group of the mercaptosilane coupling agent.

As the divinyl ether usable in the present invention, specifically divinyl ether, divinyl formal, ethyleneglycol divinyl ether, diethyleneglycol divinyl ether, triethyleneglycol divinyl ether, triethanolamine divinyl ether, 1,3-propanediol divinyl ether, 1,4-butanediol divinyl ether, 1,4-cyclohexanediol divinyl ether, 4,4'-dihydroxyazobenzene divinyl ether, hydroquinone divinyl ether, bisphenol A divinyl ether, etc. may be mentioned. Further, as trivinyl ethers, specifically glycerol trivinyl ether etc. may be mentioned. Furthermore, as tetravinyl ethers, specifically pentaerythritol tetravinyl ether etc. may be mentioned.

The silane coupling agent having a mercapto group blocked with a compound having a vinyl ether group in the present invention is a known compound. Specifically, 3-mercaptopropyl trimethoxysilane, 3-mercaptopropyl triethoxysilane, 2-mercaptoethyl trialkoxysilane, etc., which are used in the past as silane coupling agents, are preferably used. Furthermore, if 3-mercaptopropyl trimethoxysilane is used, when reacting with the silanol groups of silica, methanol is generated, and, therefore, 3-mercaptopropyl triethoxysilane is more preferable. Note that, for the rubber composition of the present invention, as the silane coupling agent, in addition to a mercaptosilane coupling agent blocked with a compound having a vinyl ether group, one or more of any silane coupling agents may be used.

The aptosilane coupling agent blocked with a compound having a vinyl ether group according to the present invention can be shown by the following formula (IV):

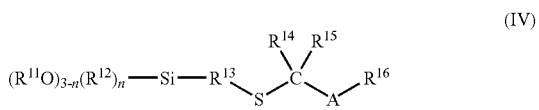

wherein n is preferably 0, 1, or 2, preferably 0, A is an oxygen atom or a sulfur atom, $R^{11}$ and $R^{12}$ may be the same or different and can be represented by $C_LH_{2L-1}$, where L=1 to 8, preferably L=1 to 2, $R^{13}$ can be represented by $C_mH_{2m}$ where m=1 to 8, preferably m=3, $R^{14}$ is a hydrogen atom or a $C_1$ to $C_{18}$, preferably a $C_1$ to $C_{10}$ alkyl group, $R^{15}$ is a hydrogen atom or a $C_1$ to $C_{18}$, preferably $C_1$ to $C_{10}$ alkyl group, a $C_2$ to $C_{18}$, preferably a $C_2$ to $C_{10}$ alkenyl group, a $C_2$ to $C_{18}$, preferably a $C_2$ to $C_{10}$ alkynyl group or a phenyl group and $R^1$ is a hydrogen atom, a $C_1$ to $C_{18}$, preferably a $C_1$ to $C_{10}$ alkyl group or a phenyl group.

The rubber composition according to the present invention may contain, in addition to the above components staple fiber such as an aramide staple fiber, a vulcanization or cross-linking agent, a vulcanization or cross-linking accelerator, various types of oils, antioxidants, plasticizers, or other various types of additives generally compounded into rubber composition for tire or others. These additives may be mixed by a general method to obtain a composition for use for vulcanization or cross-linking. The amounts of these additives may be made the conventional general amounts so long as the object of the present invention is not adversely affected.

EXAMPLES

Examples will now be used to further explain the present invention, but scope of the present invention is by no means limited to these Examples.

Examples 1 to 3, Comparative Example 1, and Reference Examples 1 to 2

Preparation of Samples

In each of the formulations shown in Table I, the ingredients other than the vulcanization accelerator and sulfur were mixed by a 1.8 liter internal mixer for 5 minutes. When reaching 150° C., the resultant mixture was discharged to obtain a master batch. To this master batch, the vulcanization accelerator and sulfur were mixed by an open roll to obtain a rubber composition. This rubber composition was used to evaluate the unvulcanized physical properties (i.e., Mooney viscosity and Mooney scorch) by the test methods shown below. The results are shown in Table I, as indexed to the values of Comparative Example 1 as 100.

Next, each obtained rubber composition was vulcanized in a 15×15×0.2 cm mold at 160° C. for 20 minutes to prepare a vulcanized rubber sheet, which was then determined by the test methods shown below for the physical properties of the vulcanized rubber (i.e., vulcanization time and ΔG'). The results are shown in Table I, as indexed to the values of Comparative Example 1 as 100.

Test Methods for Evaluation of Rubber Physical Properties

Mooney Viscosity

Viscosity at 100° C. measured according to JIS K6300. The smaller this value, the better the processability.

Mooney Scorch

Time for Mooney viscosity to increase by 5 points measured according to JIS K6300. The larger this value, the better the scorch resistance.

Vulcanization Time

Time until reaching 90% vulcanization degree at 160° C. measured according to JIS K6300. The smaller this value, the shorter the vulcanization time and the better the processability.

ΔG'

Strain shear stress G' measured using RPA2000 made by α Technology. Unvulcanized rubber used, vulcanized at 160° C.×20 minutes, and measured for G' from strain of 0.28% to 30.0, and difference ΔG'(G'0.28% (MPa)–G'30.0% (MPa)) expressed as index. The smaller this value, the better the silica dispersability.

TABLE I

| | Comp. Ex. | Ex. | | | Ref. Ex. | |
|---|---|---|---|---|---|---|
| | 1 | 1 | 2 | 3 | 1 | 2 |
| Formulation (parts by weight) | | | | | | |
| SBR | 96.25 | 96.25 | 96.25 | 96.25 | 96.25 | 96.25 |
| BR | 30 | 30 | 30 | 30 | 30 | 30 |
| SiO$_2$ | 70 | 70 | 70 | 110 | 110 | 110 |
| Carbon black | 10 | 10 | 10 | 10 | 10 | 10 |
| Stearic acid | 2 | 2 | 2 | 2 | 2 | 2 |
| Zinc white | 3 | 3 | 3 | 3 | 3 | 3 |
| Antioxidant | 1.5 | 1.5 | 1.5 | 1.5 | 1.5 | 1.5 |
| SI69 | — | — | — | — | 5.6 | 7 |
| Silane 1 | 5.6 | — | — | — | — | — |
| Silane 2 | — | 5.6 | 7 | 11 | — | — |
| Aromatic oil | 5 | 5 | 5 | 5 | 5 | 5 |
| CBS | 1.7 | 1.7 | 1.7 | 1.7 | 1.7 | 1.7 |
| Sulfur | 1.5 | 1.5 | 1.5 | 1.5 | 1.5 | 1.5 |
| DPG | 1.0 | 1.0 | 1.0 | 1.0 | 1.0 | 1.0 |
| Mooney viscosity (index) | 100 | 101 | 94 | 100 | 104 | 101 |
| Mooney scorch (index) | 100 | 123 | 110 | 102 | 135 | 130 |
| Vulcanization time (index) | 100 | 78 | 79 | 98 | 76 | 76 |
| ΔG' (index) | 100 | 84 | 80 | 99 | 116 | 110 |

Notes of Table I
SBR: VSL5025 made by Bayer
BR: Nipol 1220 made by Nippon Zeon
SiO$_2$: Zeosil 1165MP made by Rhodia
Carbon black: N234 made by Tokai Carbon
Silane 1: KBM803 made by Shin-etsu Chemical
Silane 2: Capping Mercaptosilane (see following synthesis examples)
Stearic acid: Beads Stearic Acid made by NOF Corporation
Antioxidant 6PPD: 6PPD made by Flexsys
Zinc white: Zinc Oxide Type 3 made by Seido Chemical Industry
Aromatic oil: Process X-140 made by Japan Energy
CBS: Noccelar CZ-G made by Ouchi Shinko Chemical Industrial
DPG: Noccelar D made by Ouchi Shinko Chemical Industrial
Sulfur: Oil-extended sulfur made by Tsurumi Chemical Industry Synthesis of Silane 2 (Monovinyl Ether/Mercaptosilane Block)

Mercaptosilane (KBM-803 made by Shin-Etsu Chemical) in 98.2 g (0.5 mole) and cyclohexylvinyl ether (CHVE made by Nippon Carbide Industries) in 63.1 g (0.5 mole) were made to react in the presence of a phosphoric acid ester catalyst at room temperature for 1 hour to obtain blocked mercaptosilane (KBM-803/CHVE) shown by the following formula:

$^1$H-NMR (CDCl3) σ (attribution, number of H): 0.7 (Si—CH$_2$, 2H), 1.1 to 1.4 (cyclohexyl, 10H), 1.7 (CH2, 2H), 1.8 (CH3, 3H), 2.6 (S—CH2, 2H), 3.5 (O-cyclohexyl CH, 1H), 3.6 to 3.8 (O—CH3, 9H), 4.7 (O—CH, 1H)

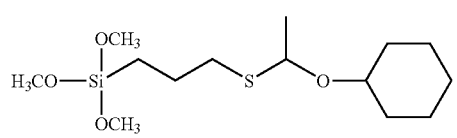

Examples 4 to 6 and Comparative Example 2

Preparation of Samples

In each of the formulations shown in Table II, the ingredients other than the vulcanization accelerator and sulfur were mixed by a 1.8 liter internal mixer for 6 minutes. When reaching 150° C., the resultant mixture was discharged to obtain a master batch. To this master batch, the vulcanization accelerator and sulfur were mixed by an open roll to obtain a rubber composition. This rubber composition was used to evaluate the unvulcanized physical properties (i.e., Mooney viscosity and Mooney scorch) by the test methods shown above. The results are shown in Table II, as indexed to the values of Comparative Example 2 as 100.

Next, each rubber composition obtained above was vulcanized in a 15×15×0.2 cm mold at 160° C. for 20 minutes to prepare a vulcanized rubber sheet which was then measured by the test methods shown below for the physical properties of the vulcanized rubber (i.e., M300/M100 and ΔG'). The results are shown in Table II, as indexed to the values of Comparative Example 2 as 100.

M300/M100

Moduli at time of 100% elongation and 300% elongation measured according to JIS K6251 and expressed as ratio of 300%/100% moduli. The larger this value, the higher the reinforcing performance of rubber by sulfur.

TABLE II

|  | Comp. Ex. | Ex. | | | |
|---|---|---|---|---|---|
|  | 2 | 4 | 5 | 6 | 7 |
| Formulation (parts by weight) | | | | | |
| SBR | 68.75 | 68.75 | 68.75 | 68.75 | 68.8 |
| BR | 25 | 25 | 25 | 25 | — |
| NR | 25 | 25 | 25 | 25 | 50.0 |
| SiO$_2$ | 75 | 75 | 75 | 75 | 100 |
| Carbon black | 10 | 10 | 10 | 10 | 5 |
| Stearic acid | 2.5 | 2.5 | 2.5 | 2.5 | 2.5 |
| Zinc white | 3 | 3 | 3 | 3 | 3 |
| Antioxidant | 2.5 | 2.5 | 2.5 | 2.5 | 2.5 |
| SI69 | — | — | — | — | — |
| Silane 1 | 6.0 | — | — | — | — |
| Silane 3 | — | 6.0 | — | 11.2 | 10.0 |
| Silane 4 | — | — | 6.0 | — | — |
| Aromatic oil | 18 | 18 | 18 | 14 | 18 |
| CBS | 2.2 | 2.2 | 2.2 | 2.2 | 2.2 |
| Sulfur | 2.0 | 2.0 | 2.0 | 2.0 | 2.0 |
| DPG | 1.0 | 1.0 | 1.0 | 1.0 | 1.0 |
| Mooney viscosity (index) | 100 | 95 | 92 | 90 | 96 |
| Mooney scorch (index) | 100 | 115 | 110 | 102 | 102 |
| M300/M100 (index) | 100 | 112 | 116 | 122 | 108 |
| ΔG' (index) | 100 | 82 | 80 | 78 | 91 |

Notes of Table II
SBR: VSL5025 made by Bayer
BR: Nipol 1220 made by Nippon Zeon
SiO$_2$: Zeosil 1165MP made by Rhodia
Carbon black: N234 made by Tokai Carbon
Silane 1: KBM803 made by Shin-etsu Chemical
Silane 3: Divinyl ether/mercaptosilane block (see following synthesis examples)
Silane 4: Trivinyl ether/mercaptosilane block (see following synthesis examples)
Stearic acid: Beads Stearic Acid made by NOF Corporation
Antioxidant 6PPD: 6PPD made by Flexsys
Zinc white: Zinc Oxide Type 3 made by Seido Chemical Industry
Aromatic oil: Process X-140 made by Japan Energy
CBS: Noccelar CZ-G made by Ouchi Shinko Chemical Industrial
DPG: Noccelar D made by Ouchi Shinko Chemical Industrial
Sulfur: Oil-extended sulfur made by Tsurumi Chemical Industry Synthesis of Silane 3 (Divinyl Ether/Mercaptosilane Block)

Mercaptosilane (KBM-803 made by Shin-Etsu Chemical) in 196.4 g (1 mole) and cyclohexane dimethanol divinyl ether (CHDVE made by Nippon Carbide Industries) in 98.2 g (0.5 mole) were reacted in the presence of a phosphoric acid ester catalyst at room temperature for 3 hours to obtain the blocked mercaptosilane of the following formula (KBM-803/CHDVE).

$^1$H-NMR (CDCl3) σ (attribution, number of H): 0.7 (Si—CH$_2$4H), 1.0 to 1.8 (cyclohexyl, 10H), 1.7 (CH$_2$, 4H), 1.8 (CH$_3$, 6H), 2.6 (S—CH$_2$, 4H), 3.2 to 3.6 (O—CH$_2$, 4H), 3.6 to 3.8 (O—CH$_3$, 18H), 4.7 (O—CH, 2H)

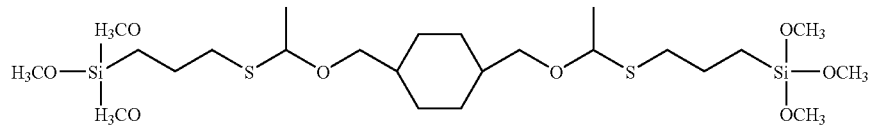

Synthesis of Silane 4 (Trivinyl Ether/Mercaptosilane Block)

Mercaptosilane (KBM-803 made by Shin-Etsu Chemical) in 196.1 g (1 mole) and trimethylol propanetrivinyl ether (TMPVE made by Nippon Carbide Industries) in 70.8 g (0.3 mole) were reacted in the presence of a phosphoric acid ester catalyst at room temperature for 8 hours to obtain the blocked mercaptosilane shown by the following formula (KBM-803/TMPVE):

$^1$H-NMR (CDCl$_3$) σ (attribution, number of H): 0.7 (Si—CH$_2$, 6H), 0.9 (CH$_2$—CH$_3$, 3H), 1.5 (C—CH$_2$, 2H), 1.7 (CH$_2$, 6H), 1.8 (CH$_3$, 9H), 2.6 (S—CH$_2$, 6H), 3.2 to 3.6 (O—CH$_2$, 6H), 3.6 to 3.8 (O—CH$_3$, 27H), 4.7 (O—CH, 3H)

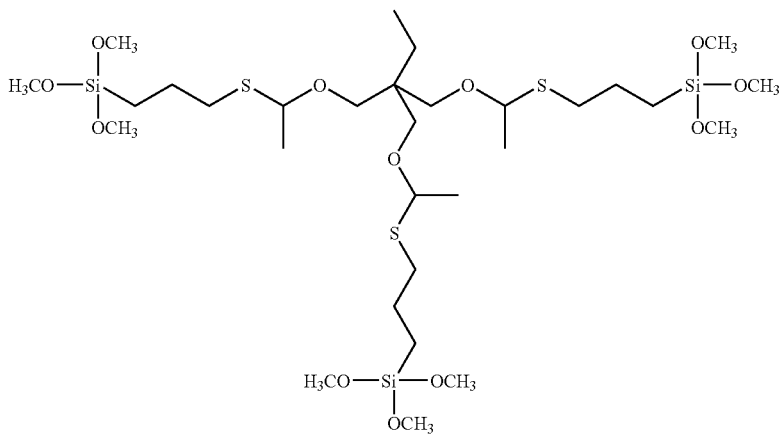

Examples 8 to 10, Comparative Example 3, and Reference Examples 1 to 2

Preparation of Samples

In each of the formulations shown in Table III, the ingredients other than the vulcanization accelerator and sulfur were mixed by a 1.8 liter internal mixer for 5 minutes. When reaching 150° C., the resultant mixture was discharged to obtain a master batch. To this master batch, the vulcanization accelerator and sulfur were mixed by an open roll to obtain a rubber composition. This rubber composition was used to evaluate the unvulcanized physical properties (i.e., Mooney viscosity and Mooney scorch) by the test methods shown below. The results are shown in Table III indexed to the values of Comparative Example 3 as 100.

Next, each obtained rubber composition was vulcanized in a 15×15×0.2 cm mold at 160° C. for 20 minutes to prepare a vulcanized rubber sheet which was then measured by the test methods shown below for the physical properties of the vulcanized rubber (i.e., vulcanization time and ΔG'). The results are shown in Table III, as indexed to the values of Comparative Example 3 as 100

Test Methods for Evaluation of Rubber Physical Properties

As explained above.

TABLE III

| | Comp. Ex. | Ex. | | | Ref. Ex. | |
|---|---|---|---|---|---|---|
| | 3 | 8 | 9 | 10 | 1 | 2 |
| Formulation (parts by weight) | | | | | | |
| SBR | 96.25 | 96.25 | 96.25 | 96.25 | 96.25 | 96.25 |
| BR | 30 | 30 | 30 | 30 | 30 | 30 |
| SiO$_2$ | 70 | 70 | 70 | 110 | 110 | 110 |
| carbon black | 10 | 10 | 10 | 10 | 10 | 10 |
| Stearic acid | 2 | 2 | 2 | 2 | 2 | 2 |
| Zinc white | 3 | 3 | 3 | 3 | 3 | 3 |
| Antioxidant | 1.5 | 1.5 | 1.5 | 1.5 | 1.5 | 1.5 |
| SI69 | — | — | — | — | 5.6 | 7 |
| Silane 1 | 5.6 | — | — | — | — | — |
| Silane 5 | — | 5.6 | 7 | 11 | — | — |
| Aromatic oil | 5 | 5 | 5 | 5 | 5 | 5 |
| CBS | 1.7 | 1.7 | 1.7 | 1.7 | 1.7 | 1.7 |
| Sulfur | 1.5 | 1.5 | 1.5 | 1.5 | 1.5 | 1.5 |
| DPG | 1.0 | 1.0 | 1.0 | 1.0 | 1.0 | 1.0 |
| Mooney viscosity (index) | 100 | 101 | 94 | 100 | 104 | 101 |
| Mooney scorch (index) | 100 | 123 | 110 | 102 | 135 | 130 |
| Vulcanization time (index) | 100 | 78 | 79 | 98 | 76 | 76 |
| ΔG' (index) | 100 | 84 | 80 | 99 | 116 | 110 |

Notes of Table III
SBR: VSL5025 made by Bayer
BR: Nipol 1220 made by Nippon Zeon
SiO$_2$: Zeosil 1165MP made by Rhodia
Carbon black: N234 made by Tokai Carbon
Silane 1: KBM803 made by Shin-etsu Chemical
Silane 5: Capping mercaptosilane block (see following synthesis examples)
Stearic acid: Beads Stearic Acid made by NOF Corporation
Antioxidant 6PPD: 6PPD made by Flexsys
Zinc white: Zinc Oxide Type 3 made by Seido Chemical Industry
Aromatic oil: Process X-140 made by Japan Energy
CBS: Noccelar CZ-G made by Ouchi Shinko Chemical Industrial
DPG: Noccelar D made by Ouchi Shinko Chemical Industrial
Sulfur: Oil-extended sulfur made by Tsurumi Chemical Industry Synthesis of Silane 5 (Monovinyl Ether/Mercaptosilane Block)

Mercaptosilane (SI263 made by Degussa) 119 g (0.5 mole) and cyclohexylvinyl ether (CHVE made by Nippon Carbide Industries) in 63.1 g (0.5 mole) were reacted in the presence of a phosphoric acid ester catalyst at room temperature for 1 hour to obtain the blocked mercaptosilane (SI263/CHVE) shown in the following formula:

$^1$H-NMR (CDCl3) σ (attribution, number of H): 0.7 (Si—CH2, 2H), 1.1 to 1.5 (cyclohexyl, 10H, —OCH$_3$, 9H), 1.7 (CH$_2$, 2H), 1.8 (CH3, 3H), 2.6 (S—CH2, 2H), 3.5 (O-cyclhexyl CH, 1H), 3.6 to 3.8 (O—CH$_2$, 6H), 4.7 (O—CH, 1H)

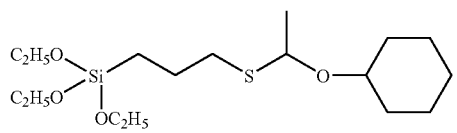

Examples 11 to 13 and Comparative Example 4

Preparation of Samples

In each of the formulations shown in Table IV, the ingredients other than the vulcanization accelerator and sulfur were mixed by a 1.8 liter internal mixer for 6 minutes. When reaching 150° C., the resultant mixture was discharged to obtain a master batch. To this master batch, the vulcanization accelerator and sulfur were mixed by an open roll to obtain a rubber composition. This rubber composition was used to evaluate the unvulcanized physical properties (i.e., Mooney viscosity and Mooney scorch) by the test methods shown above. The results are shown in Table IV, as indexed to the values of Comparative Example 4 as 100.

Next, each obtained rubber composition was vulcanized in a 15×15×0.2 cm mold at 160° C. for 20 minutes to prepare a vulcanized rubber sheet, which was then measured by the test methods shown below for the physical properties of the vulcanized rubber (i.e., M300/M100 and ΔG'). The results are shown in Table IV, as indexed to the values of Comparative Example 4 as 100.

M300/M100

Moduli at time of 100% elongation and 300% elongation measured according to JIS K6251 and expressed as ratio of 300%/100% moduli. The larger this value, the higher the reinforcing performance of rubber by sulfur.

TABLE IV

| Formulation (parts by weight) | Comp. Ex. 4 | Ex. 11 | Ex. 12 | Ex. 13 | Ex. 14 |
|---|---|---|---|---|---|
| SBR | 68.75 | 68.75 | 68.75 | 68.75 | 68.8 |
| BR | 25 | 25 | 25 | 25 | — |
| NR | 25 | 25 | 25 | 25 | 50.0 |
| SiO$_2$ | 75 | 75 | 75 | 75 | 100 |
| Carbon black | 10 | 10 | 10 | 10 | 5 |
| Stearic acid | 2.5 | 2.5 | 2.5 | 2.5 | 2.5 |
| Zinc white | 3 | 3 | 3 | 3 | 3 |
| Antioxidant | 2.5 | 2.5 | 2.5 | 2.5 | 2.5 |
| SI69 | — | — | — | — | — |
| Silane 1 | 6.0 | — | — | — | — |
| Silane 6 | — | 6.0 | — | 11.2 | 10.0 |
| Silane 7 | — | — | 6.0 | — | — |
| Aromatic oil | 18 | 18 | 18 | 14 | 18 |
| CBS | 2.2 | 2.2 | 2.2 | 2.2 | 2.2 |
| Sulfur | 2.0 | 2.0 | 2.0 | 2.0 | 2.0 |
| DPG | 1.0 | 1.0 | 1.0 | 1.0 | 1.0 |
| Mooney viscosity (index) | 100 | 95 | 92 | 90 | 96 |
| Mooney scorch (index) | 100 | 115 | 110 | 102 | 102 |
| M300/M100(index) | 100 | 112 | 116 | 122 | 108 |
| ΔG'(index) | 100 | 82 | 80 | 78 | 91 |

Notes of Table IV

SBR: VSL5025 made by Bayer

BR: Nipol 1220 made by Nippon Zeon

SiO$_2$: Zeosil 1165MP made by Rhodia

Carbon black: N234 made by Tokai Carbon

Silane 1: KBM803 made by Shin-etsu Chemical

Silane 6: Divinyl ether/mercaptosilane block (see following synthesis examples)

Silane 7: Trivinyl ether/mercaptosilane block (see following synthesis examples)

Stearic acid: Beads Stearic Acid made by NOF Corporation

Antioxidant 6PPD: 6PPD made by Flexsys

Zinc white: Zinc White Type 3 made by Seido Chemical Industry

Aromatic oil: Process X-140 made by Japan Energy

CBS: Noccelar CZ-G made by Ouchi Shinko Chemical Industrial

DPG: Noccelar D made by Ouchi Shinko Chemical Industrial

Sulfur: Oil-extended sulfur made by Tsurumi Chemical Industry

Synthesis of Silane 6 (Divinylether/Mercaptosilane Block)

Mercaptosilane (SI263 made by Degussa) in 196.4 g (1 mole) and cyclohexane dimethanol divinyl ether (CHDVE made by Nippon Carbide Industries) in 98.2 g (0.5 mole) were reacted in the presence of a phosphoric acid ester catalyst at room temperature for 3 hours to obtain a blocked mercaptosilane (SI263/CHDVE) shown by the following formula:

$^1$H-NMR (CDCl3) σ (attribution, number of H): 0.7 (Si—CH$_2$, 4H), 1.1 to 1.9 (cyclohexyl, 10H, —OCH$_3$, 18H), 1.7 (CH$_2$, 4H), 1.8 (CH$_3$, 6H), 2.6 (S—CH$_2$, 4H), 3.2 to 3.6 (O—CH$_2$, 4H), 3.6 to 3.8 (O—CH$_3$, 18H), 4.7 (O—CH, 2H)

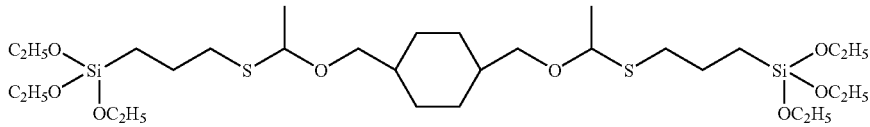

Synthesis of Silane 7 (Trivinylether/Mercaptosilane Block)

Mercaptosilane (SI263 made by Degussa) in 196.1 g (1 mole) and trimethylolpropane trivinyl ether (TMPVE made by Nippon Carbide Industries) in 70.8 g (0.3 mole) were reacted in the presence of a phosphoric acid ester catalyst at room temperature for 8 hours to obtain the blocked mercaptosilane (SI263/TMPVE) shown in the following formula:

$^1$H-NMR (CDCl3) σ (attribution, number of H): 0.7 (Si—CH$_2$, 6H), 0.9 (CH$_2$—CH$_3$, 3H), 1.5 (C—CH$_2$, 2H), 1.7 (CH$_2$, 6H), 1.8 (CH$_3$, 9H), 2.6 (S—CH$_2$, 6H), 3.2 to 3.4 (C—CH$_2$, 6H), 3.6 to 3.8 (O—CH$_2$, 18H), 4.7 (O—CH, 3H)

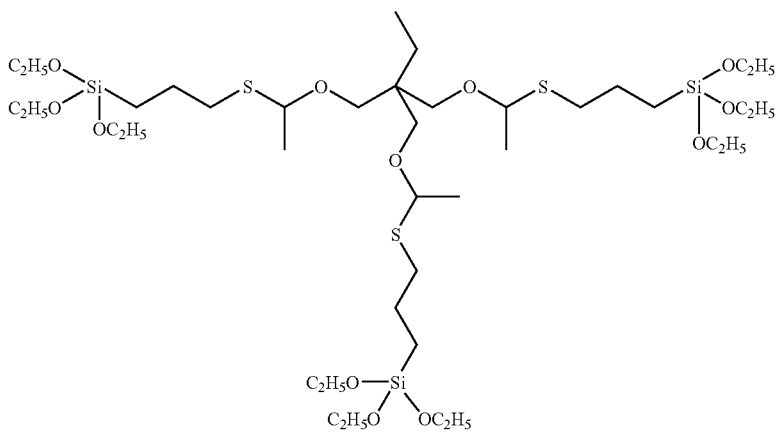

INDUSTRIAL APPLICABILITY

According to the present invention, it is possible to obtain a rubber composition having a longer scorch time and shorter vulcanization time, compared with the prior art, and to obtain a rubber composition with an excellent processability, lower ΔG', and superior dispersability of filler, and, therefore, this is useful as a tread, bead filler, side, etc. of a pneumatic tire.

The invention claimed is:

1. A rubber composition comprising 100 parts by weight of a diene-based rubber, 10 to 160 parts by weight of, a reinforcing filler including silica and 0.1 to 2000 by weight, based upon the weight of the silica, of a mercaptosilane coupling agent represented by the following formula (III):

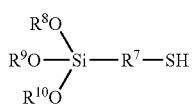

(III)

wherein $R^7$ is a $C_1$ to $C_8$ linear or branched alkylene group, $R^8$ to $R^{10}$ are, independently, a $C_1$ to $C_{18}$ linear or branched alkyl group and/or a $C_1$ to $C_{18}$ alkyl group having an ether skeleton, blocked with a compound having a vinyl ether group represented by the formula (I):

(I)

wherein A is an oxygen or sulfur atom, $R^1$ and $R^3$ are, independently, a hydrogen atom or a $C_1$ to $C_{18}$ alkyl group or a phenyl group and $R^2$ is a $C_1$ to $C_{18}$ alkyl group, a $C_2$ to $C_{18}$ alkenyl group or a $C_2$ to $C_{18}$ alkynyl group, or a phenyl group.

2. A rubber composition as claimed in claim 1, wherein the compound having a vinyl ether group of the mercaptosilane coupling agent is a polyhydric vinyl ether.

3. A rubber composition as claimed in claim 1, wherein the mercaptosilane coupling agent blocked with the compound having a vinyl ether group is represented by the following formula (IV):

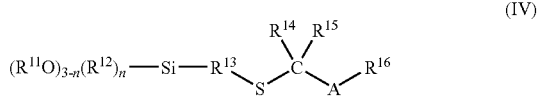

(IV)

wherein n is 0, 1, or 2, A is an oxygen atom or sulfur atom, $R^{11}$ and $R^{12}$ may be the same or different and may be represented by $C_LH_{2L-1}$ where L=1 to 8, $R^{13}$ can be represented by $C_mH_{2m}$ where m=1 to 8, $R^{14}$ indicates a hydrogen atom or a $C_1$ to $C_{18}$ alkyl group, $R^{15}$ indicates a hydrogen atom or a $C_1$ to $C_{18}$ alkyl group, a $C_2$ to $C_{18}$ alkenyl group, a $C_2$ to $C_{18}$ alkynyl group or a phenyl group and $R^{16}$ indicates a hydrogen atom, a $C_1$ to $C_{10}$ alkyl group or a phenyl group.

4. A rubber composition as claimed in claim 1, wherein the content of the silica in 10 to 160 parts by weight of the reinforcing filler is 10 to 120 parts by weight.

5. A rubber composition as claimed in claim 2, wherein the content of the silica in 10 to 160 parts by weight of the reinforcing filler is 10 to 120 parts by weight.

6. A rubber composition as claimed in claim 3, wherein the content of the silica in 10 to 160 parts by weight of the reinforcing filler is 10 to 120 parts by weight.

7. A pneumatic tire using a rubber composition according to claim 1.

8. A pneumatic tire using a rubber composition according to claim 2.

9. A pneumatic tire using a rubber composition according to claim 3.

10. A pneumatic tire using a rubber composition according to claim 4.

11. A pneumatic tire using a rubber composition according to claim 5.

12. A pneumatic tire using a rubber composition according to claim 6.

* * * * *